US008591813B2

(12) United States Patent
Munenaka

(10) Patent No.: US 8,591,813 B2
(45) Date of Patent: Nov. 26, 2013

(54) REACTION CARTRIDGE, REACTION APPARATUS AND METHOD OF MOVING SOLUTION IN REACTION CARTRIDGE

(75) Inventor: Katsumi Munenaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 1366 days.

(21) Appl. No.: 11/500,883

(22) Filed: Aug. 9, 2006

(65) Prior Publication Data

US 2007/0036679 A1 Feb. 15, 2007

(30) Foreign Application Priority Data

Aug. 15, 2005 (JP) ................................ 2005-235412

(51) Int. Cl.
*G01N 21/01* (2006.01)
*G01N 21/75* (2006.01)
*G01N 33/50* (2006.01)

(52) U.S. Cl.
USPC ............ 422/68.1; 422/81; 422/504; 422/505; 436/180

(58) Field of Classification Search
USPC .................... 422/68.1, 81, 504, 505; 436/180
See application file for complete search history.

(56) References Cited

U.S. PATENT DOCUMENTS 5,230,866 A * 7/1993 Shartle et al. ................. 422/103
5,498,392 A * 3/1996 Wilding et al. .............. 422/68.1
5,922,604 A * 7/1999 Stapleton et al. ............... 436/46
6,130,098 A * 10/2000 Handique et al. ............. 436/180
6,168,948 B1 * 1/2001 Anderson et al. .......... 435/287.2
2001/0041357 A1 * 11/2001 Fouillet et al. ............... 435/91.1
2002/0033193 A1 * 3/2002 McNeely et al. ............. 137/825
2004/0053268 A1 * 3/2004 Karlsen .............................. 435/6
2004/0092033 A1 * 5/2004 Gustafson et al. ............ 436/180
2004/0189311 A1 * 9/2004 Glezer et al. .................. 324/444
2004/0223874 A1 11/2004 Numajiri
2004/0253143 A1 12/2004 Fukushima
2006/0057740 A1 3/2006 Hiroshi et al.
2007/0077647 A1 4/2007 Munenaka ................. 435/303.1

FOREIGN PATENT DOCUMENTS

JP 2003-75444 A 3/2003
JP 3558294 5/2004
JP 2004-184180 A 7/2004
JP 2004-317498 A 11/2004
JP 2005-3637 A 1/2005
WO 93/22058 11/1993

* cited by examiner

*Primary Examiner* — Paul Hyun
(74) *Attorney, Agent, or Firm* — Fitzpatrick, Cella, Harper and Scinto

(57) ABSTRACT

A reaction cartridge comprises a first liquid reservoir having a first aperture exposed to the atmosphere and a second aperture, a first flow channel connected to the first liquid reservoir, a reaction chamber communicating with the first liquid reservoir by way of the first flow channel, a second flow channel connected to the reaction chamber and a third aperture connected to the second flow channel and exposed to the atmosphere. A probe carrier is arranged in the reaction chamber and externally supplied liquid is stored in the first liquid reservoir. The reaction cartridge is adapted to move liquid between the liquid reservoir and the reaction chamber by increasing or reducing the pressure at the third aperture.

16 Claims, 6 Drawing Sheets

REACTION CARTRIDGE, REACTION APPARATUS AND METHOD OF MOVING SOLUTION IN REACTION CARTRIDGE

BACKGROUND OF THE INVENTION

1. Field of the Invention

The present invention relates to a reaction cartridge to be used for conducting a biochemical reaction that has a reaction chamber in which a probe carrier is arranged to carry a detection probe immobilized to a substrate. More particularly, the present invention relates to a reaction cartridge to be used for conducting a biochemical reaction by using a specimen solution containing molecules of a living body that interact with a detection probe, washing liquid, air, etc., a reaction apparatus to be used for biochemical reactions and a method of moving solution in a reaction cartridge.

2. Description of the Related Art

A hybridization method is used to identify the partial sequence included in the base sequence of a nucleic acid molecule or detect the living body or bodies such as microbes contained in a specimen. With a hybridization method, it is determined whether or not a molecule of the target nucleic acid contained in a specimen specifically binds to the probe DNA whose base sequence is known in advance. Techniques are known for utilizing a probe array (also referred to as micro-array) that is formed by regularly arranging regions (probe spots) where probe DNAs of a plurality of different types are respectively immobilized on a substrate for the purpose of conducting a hybridization method accurately and effectively. With such a technique, it is possible to carry out detecting operations concurrently for a plurality of items because it is possible to determine whether molecules in the specimen bind to the probe DNAs of a plurality of different types. With a hybridization method using such a micro-array, bio-polymers in a solution are subjected to hybridization with the probes arranged regularly on a substrate for analysis such as detection and quantification of a target nucleic acid. For a hybridization reaction, hybridization solution is filled into a reaction chamber comprising as a component a a substrate where probes are immobilized and the substrate is held at a constant temperature for a long time. FIG. 5 of the accompanying drawings schematically illustrates a reaction apparatus and a reaction cartridge disclosed in Japanese Patent No. 3558294 as conventional art. The above-cited document discloses a technique of injecting liquid into a cartridge 12 through an injection port formed in the substrate of the cartridge 12 by way of a pump 52.

When injecting liquid into the cartridge 12, firstly the cartridge 12 is fitted to a containing site 58 arranged in the reaction apparatus 50. The, as a result, a closed space is produced to run from the pump 52 to a port 59 arranged in the reaction apparatus by way of the cartridge 12. No gap should be produced between apertures 23, 24 arranged in the cartridge and a flow channel 56. The liquid injected into the liquid injection port 51 arranged in the reaction apparatus 50 moves into the flow channel 56 when the port 59 is exposed to the atmosphere and the pump 52 is operated.

The liquid that has moved into the flow channel 56 then passes through the aperture 23 by way of the pump 52 and is injected into injection port 16 in the inside of the cartridge 12. The liquid that has been injected into the injection port 16 then moves into a reaction chamber 22 by way of a flow channel 20 arranged in the inside of the cartridge 12. The internal temperature of the reaction chamber 22 is held to the level suitable for the reaction by means of a temperature regulator 57. When the substance and/or the waste liquid produced in the reaction chamber 22 needs to be taken out, it can be done so by moving the liquid from the cartridge 12 to the port 59.

The internal pressure in each of the flow channels in the reaction apparatus 50 and the cartridge 12 rises when the pump is operated. If the reaction apparatus 50 and/or the cartridge 12 is clogged and consequently the internal pressure rises or falls extremely there, the rise or the fall, whichever appropriate, is detected by either or both of the two pressure detectors 54 so that the operation of the pump can be stopped.

A particular care needs to be taken when examining genes extracted from a blood specimen or the like since the specimen may be contaminated by some other specimen to give rise to examination errors.

However, when the above-described conventional art is used and liquid is injected into the cartridge by way of the pump, the liquid passes by the inner wall of the pump. In other words, the inner wall of the pump is exposed to any liquid that passes there. Thus, if the inside of the pump is thoroughly washed and cleaned, the problem of contamination by some other specimen can occur.

Additionally, with the conventional art, liquid is driven to move by applying positive pressure to the injection port of the cartridge. Therefore, the apparatus can be damaged and liquid can leak unless the operation of the apparatus is stopped immediately when a trouble such as clogging occurs. Thus, the apparatus has to be provided with a pressure sensor or similar instrument.

SUMMARY OF THE INVENTION

In view of the above-identified circumstances, it is therefore an object of the present invention to provide a reaction apparatus that can supply liquids of a plurality of different types or quantities to a reaction chamber whenever necessary and, at the same time, has a simple configuration.

According to the present invention, the above object is achieved by providing a reaction cartridge comprising: a first liquid reservoir having a first aperture exposed to the atmosphere and a second aperture; a first flow channel connected to the first liquid reservoir; a reaction chamber communicating with the first liquid reservoir by way of the first flow channel; a second flow channel connected to the reaction chamber; and a third aperture connected to the second flow channel and exposed to the atmosphere, a probe carrier being arranged in the reaction chamber, externally supplied liquid being stored in the first liquid reservoir, the reaction cartridge being adapted to move the liquid between the liquid reservoir and the reaction chamber by increasing or reducing the pressure at the third aperture.

Thus, according to the present invention, it is possible to remarkably reduce the risk of mutual contamination of different solutions. Additionally, it is not necessary to provide a pressure sensor and hence the reaction cartridge can be made to show a simple structure.

Further features of the present invention will become apparent from the following description of exemplary embodiments with reference to the attached drawings.

DESCRIPTION OF THE EMBODIMENTS

Figure 1:
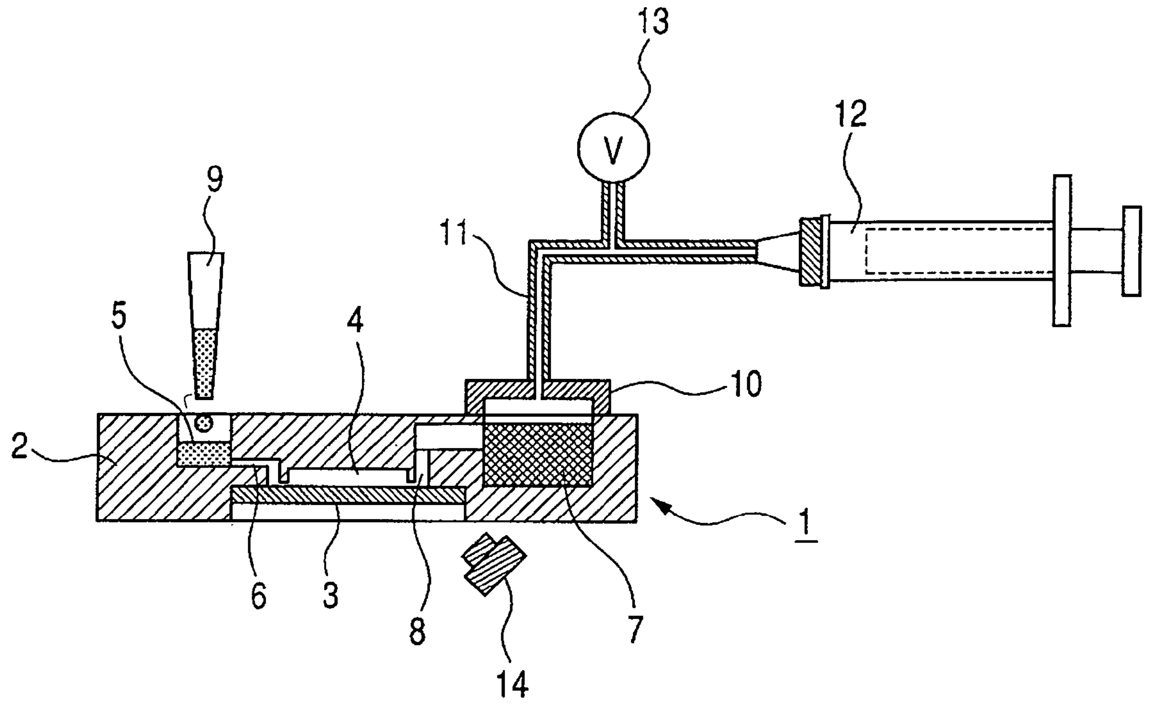
FIG. 1 is a schematic cross sectional view of a principal part of the second embodiment of reaction cartridge according to the present invention.

Preferred embodiments of the present invention will now be described in detail in accordance with the accompanying drawings.

A reaction cartridge to be used for conducting a biochemical reaction according to the invention comprises: a first liquid reservoir having a first aperture exposed to the atmosphere and a second aperture; a first flow channel connected to the first liquid reservoir; a reaction chamber communicating with the first liquid reservoir by way of the first flow channel; a second flow channel connected to the reaction chamber; and a third aperture connected to the second flow channel and exposed to the atmosphere, a probe carrier being arranged in the reaction chamber, externally supplied liquid being stored in the first liquid reservoir, the reaction cartridge being adapted to move the liquid between the liquid reservoir and the reaction chamber by increasing or reducing the pressure at the third aperture.

In a specific embodiment of the present invention, a first liquid reservoir having an end exposed to the atmosphere and a first flow channel connected to the first liquid reservoir are formed on a substrate. Additionally, a reaction chamber held in communication with the first liquid reservoir by way of the first flow channel, a second flow channel connected to the reaction chamber, and a second liquid reservoir are formed. The reaction chamber is characterized in that a probe carrier that immobilizes probes, each of which can specifically bind to a specific target substance, can be mounted therein.

The reaction cartridge may be so formed as to contain a probe carrier preferably in such a way that the second aperture of the reaction chamber is closed by the probe carrier. The probe carrier may be arranged in the reaction chamber.

Substances that can be used for the probe include oligo nucleotides, polynucleotides and other polymers that can recognize a specific target. The term "probe" refers to a molecule that can operate as probe such as an individual polynucleotide molecule or a group of molecules such as polynucleotide molecules having the same sequence and immobilized at dispersed positions on the surface of the carrier and can operate as so many identical probes. A molecule that is often called ligand can also operate as probe. Probes and targets of probes are often replaceably used. Probes can bind to respective targets or changed to become able to bind to respective targets and operate as part of ligand-antiligand (or ligand-receptor) pairs. Probes and targets may include bases found in nature and similar substances.

Examples of probes adapted to be supported on a substrate include those having a part of oligonucleotide showing a base sequence capable of hybridizing with the target nucleic acid and provided with a bonding site capable of bonding itself to a substrate by way of a linker. Thus, such a probe has a structure linked to the surface of a substrate at the bonding site where it is bonded to the substrate. Preferably, probes are single-stranded nucleic acids having a base sequence that is complementary relative to all or part of the target nucleic acid and are capable of specifically hybridize with the target nucleic acid. With such an arrangement, the location of the bonding site in the oligonucleotide where it is bonded to the substrate is not particularly limited so long as the location does not adversely affect the desired hybridization reaction.

The probes to be used with the probe carrier may be appropriately selected depending on the purpose of the use. However, the probes are preferably selected from DNAs, RNAs, cDNAs (complementary DNAs), PNAs, oligonucleotides, polynucleotides, other nucleic acids, oligopeptides, polypeptides, proteins, enzymes, substrates for enzymes, antibodies, epitopes for antibodies, antigens, hormones, hormone receptors, ligands, ligand receptors, oligosaccharides and polysaccharides. If necessary, any two of these may be combined for use. A probe carrier is formed by immobilizing probes of a plurality of different types on the surface of a substrate (which may include the inner wall surface of a hollow body or an annular carrier) to produce independent regions (e.g., dotted spots). A probe carrier formed by arranging probes at regular intervals may also be referred to as probe array.

Materials that can be used for probes have a structure capable of being bonded to a substrate and it is desirable that they are bonded to a substrate by utilizing the structure that is capable of being coupled to a substrate after discharging and applying a probe solution. Such a structure that makes it possible to bond the material to a substrate can be formed by introducing organic functional groups selected from amino group, mercapto group, carboxyl group, hydroxyl group, acid halide (—COX), halide, aziridine, maleimide, succinimide, isothiocyanate, sulfonyl chloride (—$SO_2Cl$), aldehyde(—CHO), hydrazine and acetamide iodide into the molecules of the probe materials in advance. Then, it is necessary to process the surface of the substrate in advance in order to introduce a structure (organic function groups) capable of reacting with any of various organic functional groups to form covalent bonds. For example, when a probe material contains molecules having an amino group, succinimide ester, isothiocyanate, solfonyl chloride or aldehyde can be introduced to the surface of the substrate. When a probe material contains mercapto groups (thiol groups), maleimide can be introduced to the surface of the substrate. When a glass substrate is used as substrate, it is possible to introduce desired functional groups to the surface of the substrate by means of a silane coupling agent having desired functional groups and additionally a cross-linking agent or the like having desired functional groups.

In this embodiment of the present invention, the first liquid reservoir, the second liquid reservoir, the reaction chamber, the first flow channel that keeps the first liquid reservoir and the reaction chamber in communication with each other, and the second flow channel that keeps the reaction chamber and the second liquid reservoir in communication with each other are formed in the cartridge.

These flow channels may be formed by arranging through bores running through the substrate or by stacking substrates where grooves are formed one on the other.

When solution that contains a specimen is supplied to the first liquid reservoir and the waste liquid produced after causing the specimen to react with the probe carrier in the reaction chamber is discharged into the second liquid reservoir, an absorbent may preferably be arranged in the second liquid reservoir (waste liquid reservoir) in order to absorb waste liquid. With such an arrangement, it is possible to prevent waste liquid from jumping out through the open end of the second liquid reservoir if the supplied solution is moved violently.

In this embodiment, when the solution containing a specimen that is supplied to the first liquid reservoir is to be moved into the reaction chamber, it is important that a pressure can be applied to the second liquid reservoir and that one of the opposite ends of the first liquid reservoir is open. With such an arrangement, it is possible to drive the solution to move into the reaction chamber by the pressure application means that can apply pressure to the open end of the second liquid reservoir.

More specifically, when the solution supplied to the first liquid reservoir is to be moved into the reaction chamber, it can actually be moved into the reaction chamber by holding the reaction cartridge by a cartridge holding means and reduce the internal pressure of the second liquid reservoir by way of the open end thereof to bring the inside of the second liquid reservoir under negative pressure. When conversely the solution that has been moved into the reaction chamber is to be moved back into the first liquid reservoir, it can actually be moved back by applying positive pressure to the open end of the second liquid reservoir. Since the first liquid reservoir, the reaction chamber and the second liquid reservoir are linked in the above mentioned order, negative pressure should be applied to the open end of the second liquid reservoir to move the solution in the first liquid reservoir toward the second liquid reservoir. Conversely, positive pressure should be applied to the open end of the second liquid reservoir to move the solution in the second liquid reservoir toward the first liquid reservoir.

For the purpose of the present invention, pressure may be applied by means of a pump or the like, which is preferably a syringe pump. A syringe pump is adapted to apply pressure at a constant pressure level by driving the plunger at a constant speed by means of a high performance motor. Therefore, a syringe pump is suitable for feeding liquid highly accurately at a constant fine flow rate as a non-pulsating flow. However, a pump other than a syringe pump may alternatively be used for the purpose of the present invention so long as it can feed liquid at a constant fine flow rate.

The pump is stopped to stop the movement of the solution. In the case of a syringe pump, the pump is stopped by stopping the movement of the plunger. However, there is a slight time lag between the time when the plunger is stopped and the time when the solution stops moving. Therefore, a valve is preferably provided between the pump that operates as a pressure application means and the second liquid reservoir as a means for regulating the pressure and restoring the atmospheric pressure. Then, the movement of the solution can be stopped by opening the valve simultaneously with the stop of the pump operation and causing the open end of the second liquid reservoir to restore the atmospheric pressure.

Preferably, a detection means is provided to detect the presence or absence of solution in the reaction chamber for the purpose of maintaining a constant moving speed of liquid. The accuracy of detection can be improved by directly monitoring the quantity of liquid in the reaction chamber. It is also possible to predict the quantity of liquid supplied to the reaction chamber by the moving time of liquid.

Figure 8A:
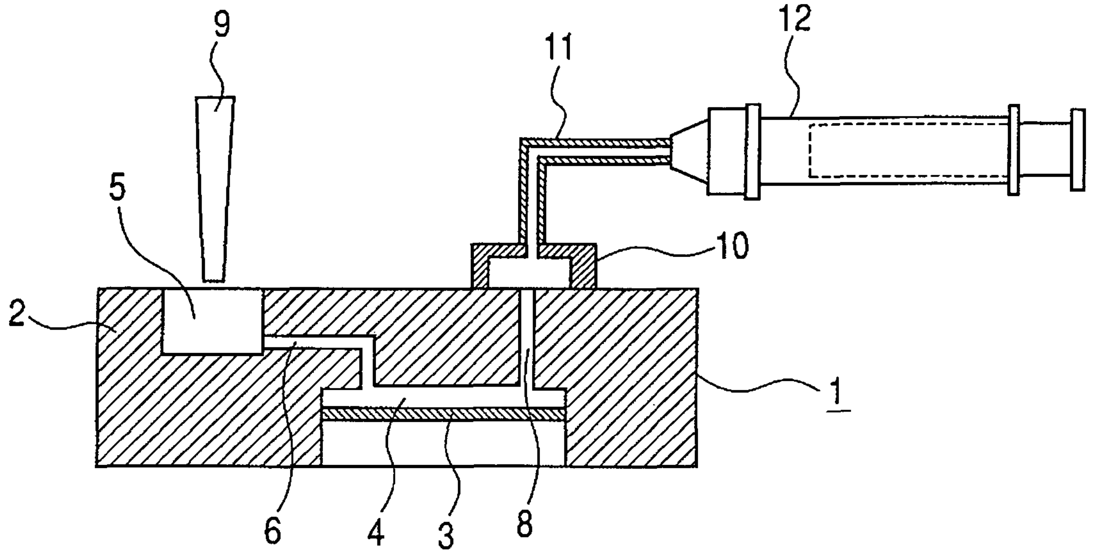
FIGS. 8A and 8B are schematic cross sectional views of a reaction cartridge according to the present invention, illustrating the underlying principle thereof.
Figure 8B:
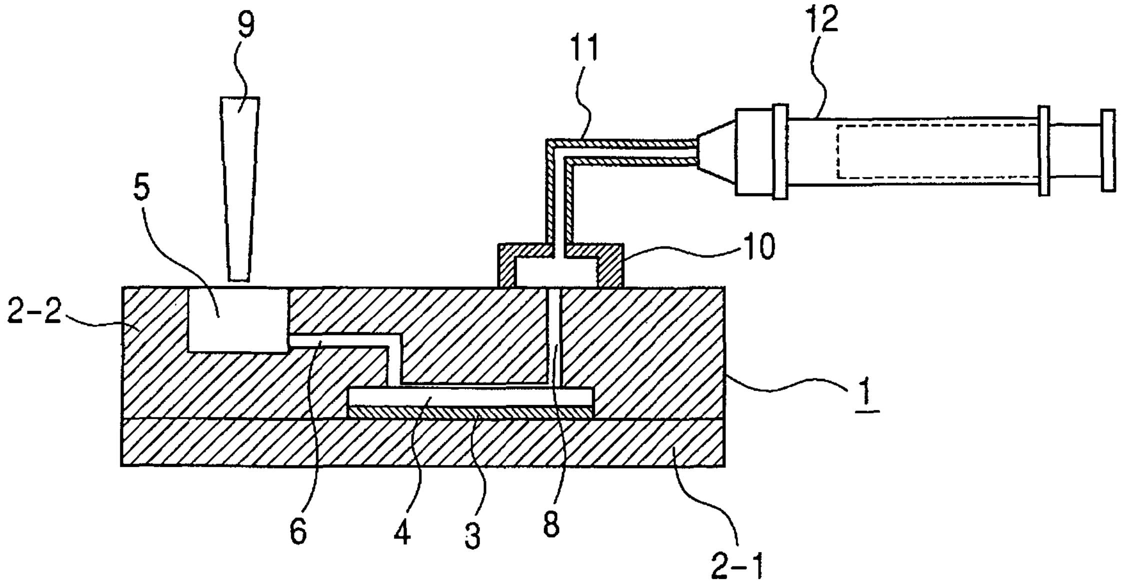

FIGS. 8A and 8B are schematic cross sectional views of the first embodiment of reaction cartridge according to the present invention that is adapted to be used for a biochemical reaction. The reaction cartridge 1 of FIG. 8A comprises a substrate 2 made of a resin material such as polysulfone or polycarbonate, where a liquid reservoir 5, a reaction chamber 4, a first flow channel 6 for keeping the liquid reservoir 5 and the reaction chamber 4 in communication with each other and a second flow channel 8 open to the atmosphere by way of an aperture for exposing the reaction chamber 4 to the atmosphere are formed.

The aperture section of the second flow channel 8 that is exposed to the atmosphere is provided with a syringe pump 12 by way of a cap 10 and a tube 11. The cap 10 is provided to airtightly seal the aperture section of the second flow channel 8 that is exposed to the atmosphere. The liquid reservoir 5 is exposed to the atmosphere at an end thereof and a pipette 9 is arranged vis-à-vis the open end to supply liquid to the liquid reservoir 5.

The reaction cartridge of FIG. 8B is formed by modifying that of FIG. 8A. The reaction cartridge of FIG. 8B comprises a substrate 2-2, where a liquid reservoir 5, a reaction chamber 4, a first flow channel 6 keeping the liquid reservoir 5 and the reaction chamber 4 in communication with each other and a second flow channel 8 open to the atmosphere by way of an aperture for exposing the reaction chamber 4 to the atmosphere are formed. The reaction cartridge 1 is formed by bonding the substrate 2-2 and another substrate 2-1 where a probe carrier is mounted. The reaction chamber 4 formed in the substrate 2-2 is open at the side of the substrate 2-2 facing the substrate 2-1.

As in FIG. 8A, the aperture section of the second flow channel 8 that is exposed to the atmosphere is provided with a syringe pump 12 by way of a cap 10 and a tube 11. The cap 10 is provided to airtightly seal the aperture section of the second flow channel 8 that is exposed to the atmosphere. The liquid reservoir 5 is exposed to the atmosphere at an end thereof and a pipette 9 is arranged vis-à-vis the open end to supply liquid to the liquid reservoir 5.

Thus, the pipette 9 is arranged at the open end of the liquid reservoir 5 to supply liquid to the liquid reservoir 5. The aperture section for exposing the second flow channel 8 to the atmosphere is covered by the cap 10 connected to the syringe pump 12 by way of the tube 11.

Figure 9A:
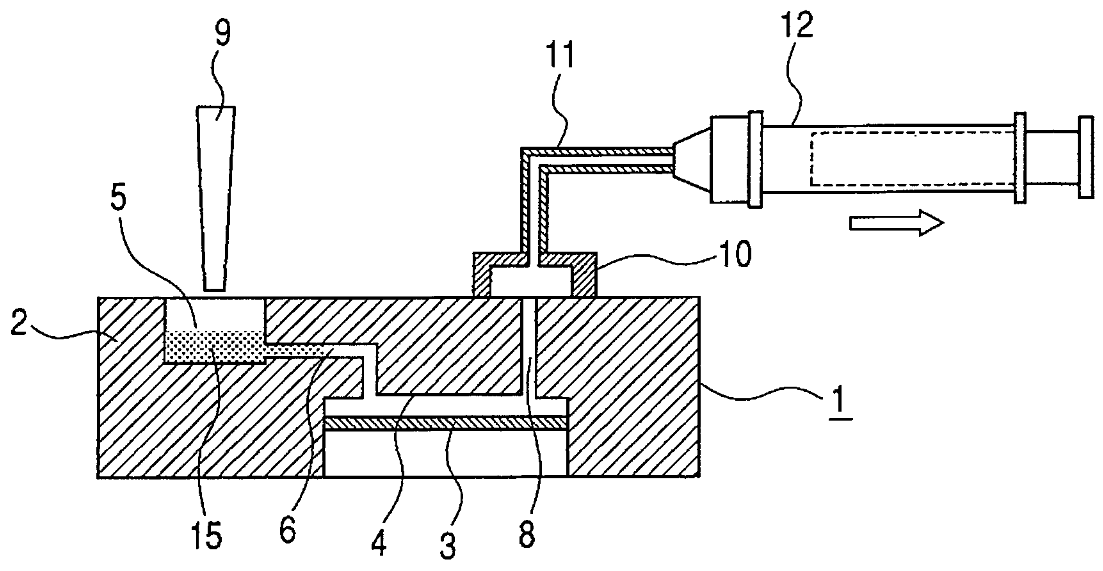
FIGS. 9A and 9B are schematic cross sectional views of a reaction cartridge according to the present invention, illustrating the principle of moving liquid in it.

Now, the operation of moving liquid in the reaction cartridge 1 will be described below by referring to FIGS. 9A and 9B. Referring firstly to FIG. 9A, as the liquid 15 supplied from the pipette 9 is fed to the liquid reservoir 5 to cover the aperture that communicates with the first flow channel of the liquid reservoir, the first flow channel 6, the reaction chamber 4 and the second flow channel 8 produce a space that is closed at an end. As the plunger of the syringe pump 12 is moved in the direction of an arrow (to the right side) in FIG. 9A under this condition, the pressure at the aperture section of the second flow channel 8 that is exposed to the atmosphere is reduced. Then, as a result, it is possible to move the liquid 15 fed into the liquid reservoir 5 into the reaction chamber 4 by way of the first flow channel 6.

The liquid flow rate for supplying liquid from the liquid reservoir 5 is preferably lower than or the same as the liquid flow rate for supplying liquid to the liquid reservoir 5 in order to move the liquid 15 continuously.

Figure 9B:
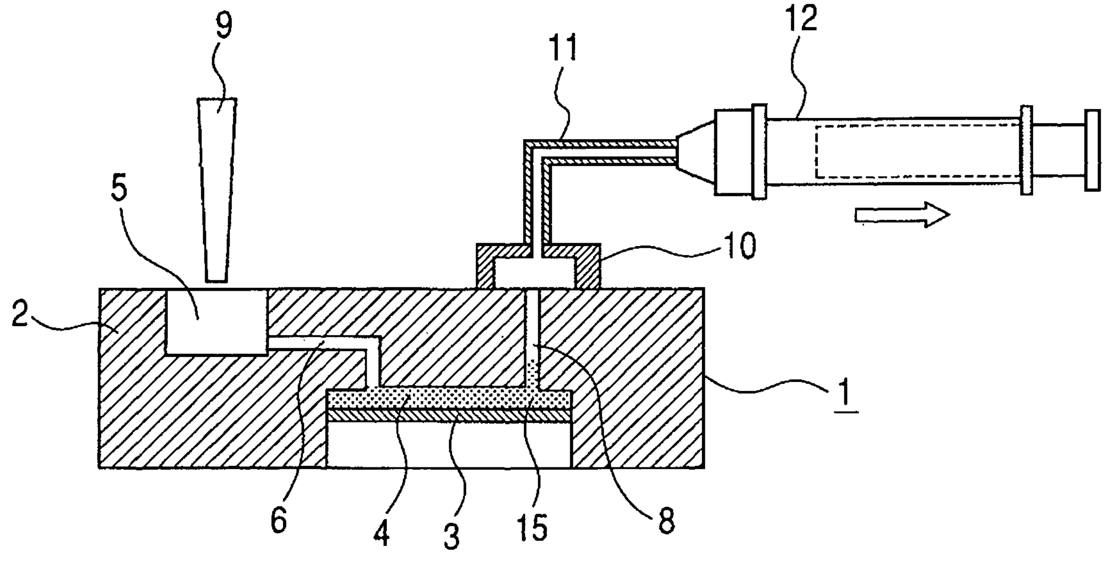

As shown in FIG. 9B, as liquid 15 moves into the reaction chamber 4, the reaction chamber 4 is constantly filled with the injected liquid because the reaction chamber 4 has a very small height (normally, between 0.05 mm and 2.0 mm, preferably between 0.1 mm and 1.0 mm). Then, it is possible to move the liquid 15 fed into the reaction chamber 4 by way of the second flow channel by moving the plunger of the syringe pump 12 further in the direction of the arrow (to the right side) in FIG. 9B under this condition. Although not shown, a waste reservoir may be arranged between the aperture of the second flow channel that communicates with the reaction chamber and the aperture thereof exposed to the atmosphere.

Figure 10A:
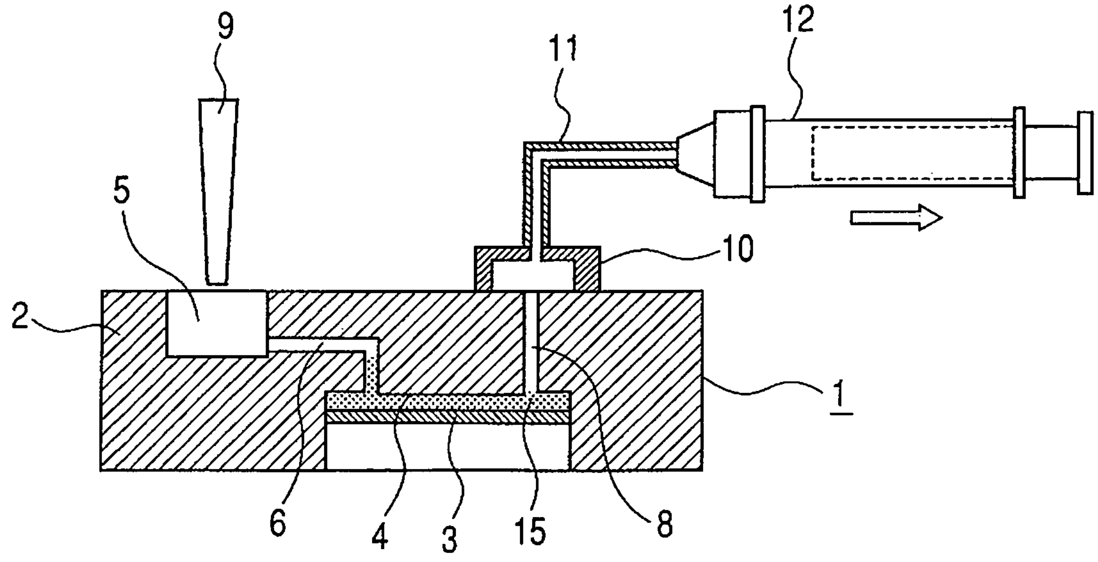
FIGS. 10A and 10B are schematic cross sectional views of a reaction cartridge according to the present invention, illustrating the principle of moving liquid in it.

Now, the operation of agitating liquid in the reaction chamber will be described below by referring to FIGS. 10A and 10B. Referring firstly to FIG. 10A, as the plunger of the syringe pump 12 is moved in the direction of the arrow (to the left side) in FIG. 10A under the condition where the reaction chamber 4 is filled with liquid, the aperture section of the second flow channel 8 that is exposed to the atmosphere is pressurized. As a result, the liquid 15 supplied to the reaction chamber 4 moves toward the first flow channel 6.

Thus, it is possible to agitate the liquid by alternately producing a pressurized condition and a reduced pressure condition. The probe carrier 3 mounted in the reaction chamber 4 reacts with the solution (liquid 15) that contains the nucleic acid of the specimen. It is preferable to cause the probe carrier 3 and the solution (liquid 15) that contains the nucleic acid of the specimen to react with each other while agitating the solution on the probe carrier 3 in order to make the reaction proceed uniformly.

Figure 10B:
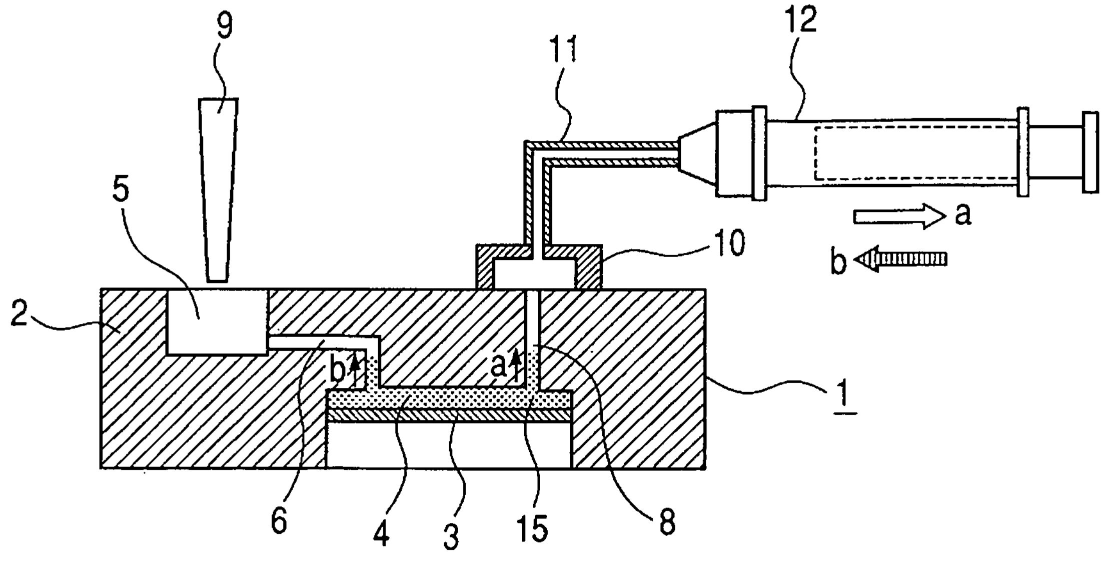

Now, as the plunger of the syringe pump 12 is moved in the direction of the arrow a (to the right side) in FIG. 10B, the liquid 15 in the reaction chamber moves into the second flow channel in the direction of the arrow a in FIG. 10B. On the other hand, as the plunger of the syringe pump 12 is moved in the direction of the arrow b (to the left side) in FIG. 10B, the liquid 15 in the reaction chamber moves into the first flow channel in the direction of arrow b in FIG. 10B. It is possible to agitate the liquid 15 in the reaction chamber by alternately moving the liquid in opposite directions.

It is possible to move the liquid in the second flow channel 8 at a constant flow rate by controlling the pressure of the aperture section of the second flow channel 8 that is exposed to the atmosphere to show a constant reduced pressure condition or a constant pressurized condition. In the case of a syringe pump, the flow rate can be controlled to a constant level by moving the plunger at a constant speed. Additionally, the quantity of liquid to be moved can be controlled by controlling the distance by which the plunger is moved.

Now, the second embodiment of the present invention will be described also by referring to the related drawings.

FIG. 1 is a schematic cross sectional view of a principal part of the second embodiment of reaction cartridge according to the present invention that constitutes part of a liquid control apparatus and is adapted to be used for biochemical reactions, showing components of the apparatus main body.

The reaction cartridge 1 comprises a substrate 2 made of a resin material such as polysulfone or polycarbonate and a probe carrier 3. A liquid reservoir 5, a reaction chamber 4, a waste liquid reservoir 7, a flow channel 6 keeping a liquid reservoir 5 and a reaction chamber 4 in communication with each other and another flow channel 8 keeping the reaction chamber 4 and the waste liquid reservoir 7 in communication with each other are formed in the substrate 2. The liquid reservoir 5 and the waste liquid reservoir 7 are exposed to the atmosphere at an end thereof.

An absorbent is arranged in the inside of the waste liquid reservoir 7. The absorbent may be a fibrous absorbent, a polymer absorbent, a powdery absorbent or a sheet-shaped absorbent. The absorbent may be made of any material that does not react with the specimen to be used for a biochemical reaction and other solutions. While the absorbent is made of PP (polypropylene) fiber in this embodiment, the material of the absorbent is not limited to PP fiber so long as it can meet the above requirement.

Figure 6:
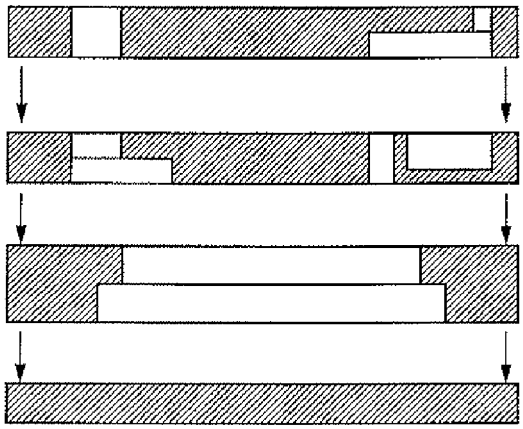
FIG. 6 is a schematic illustration of a reaction cartridge according to the present invention, showing the configuration of the substrate thereof.

The reaction cartridge 1 is typically formed by stacking substrates as shown in FIG. 6 one on the other.

A pipette 9 is arranged at the side of the reaction apparatus main body so as to be independent from the reaction cartridge 1. The pipette 9 operates to take a necessary quantity of the solution required for the reaction or process of the probe of the probe carrier 3 such as hybridization solution or washing liquid from a solution stocker (not shown) arranged in the apparatus main body and inject it into the liquid reservoir 5 arranged in the reaction cartridge 1.

If the item of examination remains the same, the solution to be injected into the reaction cartridge should be replaced by another one each time of examination when it is a specimen but it may not be replaced when it is reaction solution or washing liquid. While all the solution is dispensed by means of the pipette in the description of this embodiment, a specimen may be dispensed by a necessary any each time of examination, whereas reaction solution or washing liquid may be injected into the liquid reservoir 5 from a container that contains the solution by a given quantity by means of a pump. For the purpose of the present invention, the pump is preferably a syringe pump because it can feed liquid highly accurately at a constant fine flow rate.

When the pipette is driven to operate by electric power, it is possible to operate it by way of a microprocessor.

The cap 10 is connected to the front end of the tube 11. A valve 13 is arranged midway of the tube 11 to make it possible to expose the space extending between the waste liquid reservoir 7 and the syringe pump 12 to the atmosphere.

While a syringe pump is used in this embodiment, a pump other than a syringe pump such as a rotary pump may alternatively be used for the purpose of the present invention so long as it can feed liquid at a constant fine flow rate. However, a syringe pump is adapted to feed liquid highly accurately at a constant fine flow rate as a non-pulsating flow by driving the plunger of the syringe at a constant speed by means of a high performance motor (not shown) that is controlled by a microprocessor (not shown). Therefore, a syringe pump is suitable for the purpose of the present invention.

For example, it is possible to control the flow rate between 0.0014 μl/h and 53.12 ml/min by means of a Harvard Syringe Pump Model 11.

The speed of supplying solution to the liquid reservoir 5 and the speed of moving solution from the liquid reservoir 5 to the reaction chamber 4, from the reaction chamber 4 to the liquid reservoir 5 or from the liquid reservoir 5 to the waste liquid reservoir 7 by way of the reaction chamber 5 can be held to a constant level by means of a syringe pump.

Figure 2:
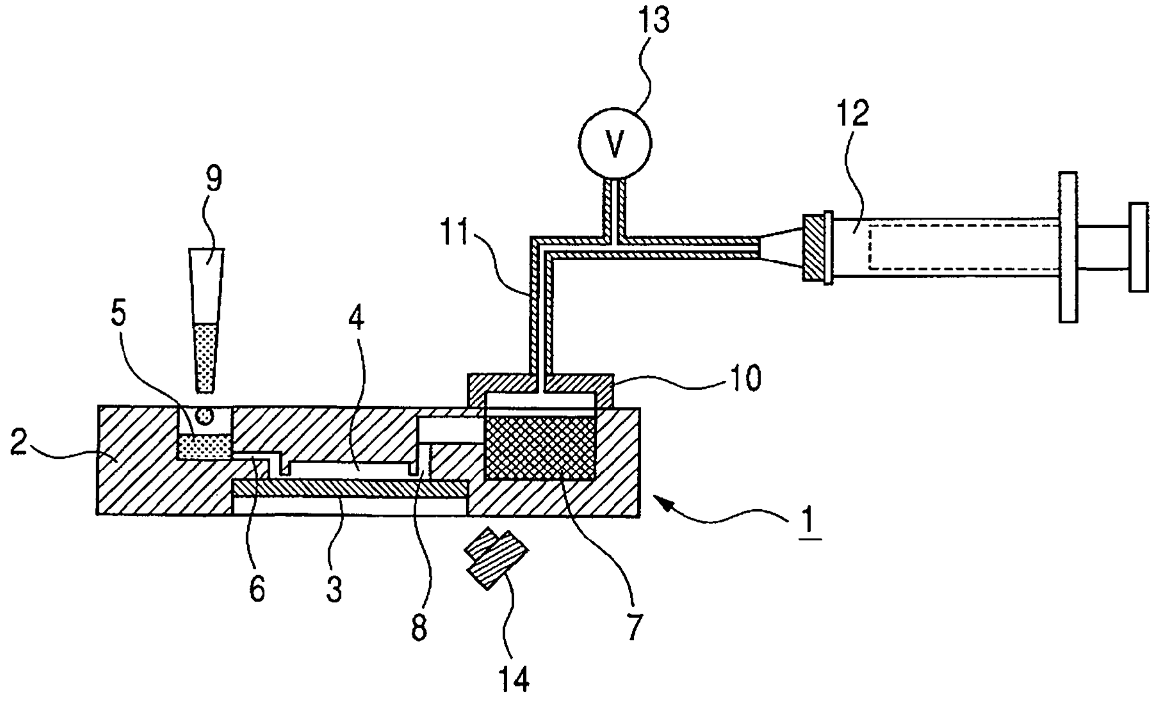
FIG. 2 is a schematic illustration of the operation of supplying solution of the second embodiment of reaction cartridge according to the present invention.
Figure 7:
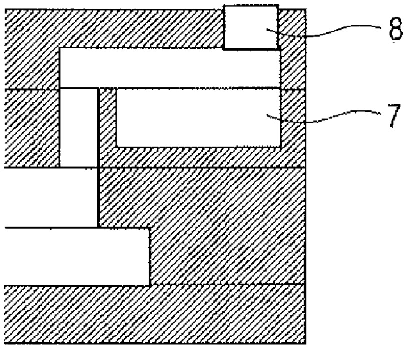
FIG. 7 is an enlarged schematic view of a modified second liquid reservoir (waste liquid reservoir) of the first embodiment of the present invention.

FIG. 7 is an enlarged schematic view of the waste liquid reservoir of this embodiment. When the waste liquid reservoir 7 has a profile as shown in FIG. 7, it is provided at a surface thereof with an aperture 8 but can be airtightly sealed by putting a cap 10 for connecting it to the syringe pump 12 into the aperture 8 of the waste liquid reservoir 7. While the waste liquid reservoir 7 is provided with an aperture so as to expose the entire inner wall of the waste liquid reservoir 7 to the atmosphere in FIG. 1, the waste liquid reservoir 7 may alternatively be provided at part of the inner wall thereof with an aperture as shown in FIG. 7. FIG. 2 illustrates how solution is supplied to the liquid reservoir 5 by means of the pipette 9. The cap 10 is tightly fitted to the aperture of the waste liquid reservoir. Since the valve 13 is closed, the space extending between the waste liquid reservoir 7 and the syringe pump 12, or the flow channel downstream relative to the liquid reservoir 5, is closed to the atmosphere. Therefore, the solution supplied to the liquid reservoir 5 would never flow into the flow channel 6. Since the pipette 9 operates to dispense a predetermined quantity of liquid, it is possible to supply the solution by a necessary quantity to the liquid reservoir 5.

Figure 3:
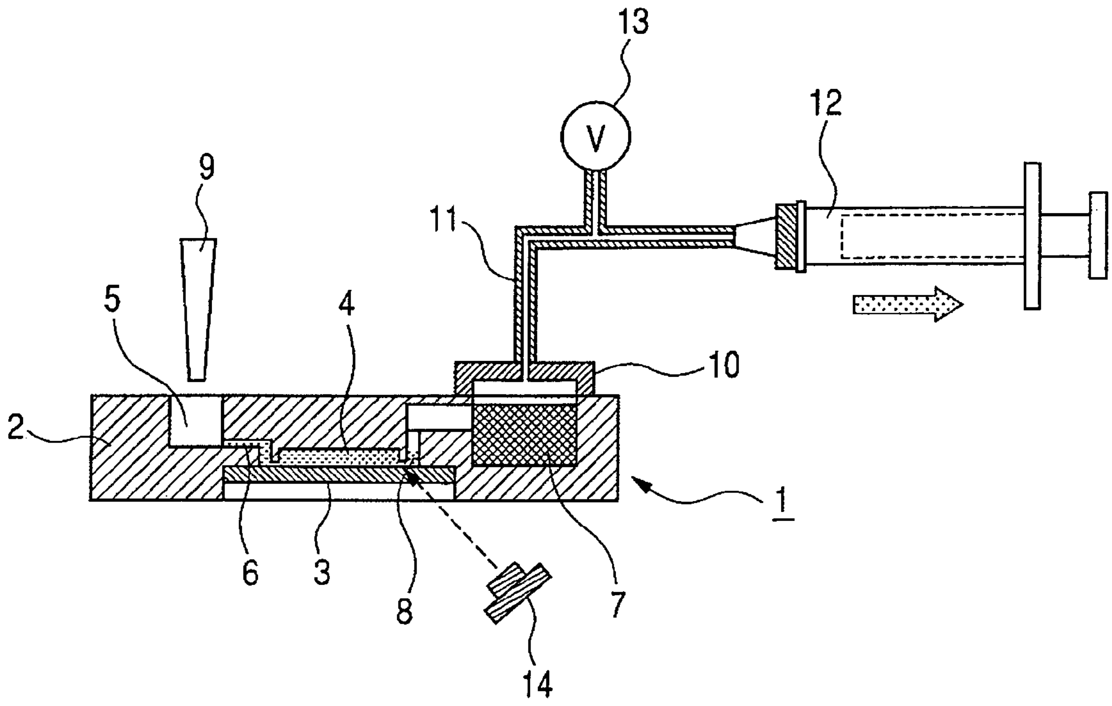
FIG. 3 is a schematic illustration of the operation of moving solution of the second embodiment of reaction cartridge according to the present invention.

FIG. 3 shows how negative pressure is applied to the reaction chamber 4 by means of the syringe pump 12 and move solution from the liquid reservoir 5 to the reaction chamber 4 after supplying solution to the liquid reservoir 5 by means of the pipette 9. The flow channel is monitored at reaction chamber 4 or at the outlet or near the outlet of the reaction chamber 4 by means of a photo-sensor 14 arranged at the side of the apparatus main body. Thus, the operation of driving the syringe pump 12 is stopped when it is determined that the reaction chamber 4 is filled with the liquid that has been moved in it.

In this way, solution is moved from the inside of the liquid reservoir 5 to the reaction chamber 4 efficiently and accurately by a control means (not shown) that controls the function of detecting the solution being filled of the photo-sensor 14 and the function of supplying liquid at a constant rate of the syringe pump 12.

When the substrate 2 is made of a transparent or translucent material such as polysulfone or polycarbonate and the condition of the reaction chamber 4 being filled with solution is detected by means of the photo-sensor 14, light is irradiated onto the reaction chamber 4 from the outside and light reflected by the reaction chamber 4 is observed by means of a light receiving element. Alternatively, the solution being injected into the reaction chamber 4 can be directly monitored and detected by means of a two-dimensional light receiving element such as CCDs (charge coupled devices).

The movement of solution can be stopped quickly by stopping the operation of the syringe pump 12 when it is detected by the photo-sensor 14 that a predetermined quantity of solution is injected into the reaction chamber 4 and, at the same time, opening the valve 13 arranged between the syringe pump 12 and the open end of the waste liquid reservoir 7.

In this embodiment, the solution may be replaced sequentially and supplied from the pipette 9 so that it is possible to supply liquids of a plurality of different types from a single supply aperture without providing a plurality of liquid reservoirs when supplying liquids of a plurality of different types to the reaction chamber.

More specifically, the first solution that contains a specimen of nucleic acid is supplied into the reaction chamber and the reaction cartridge 1 is held at a predetermined temperature for a predetermined time period in order to give rise to a hybridization reaction between the probe nucleic acid of the probe carrier 3 and the nucleic acid of the specimen. Subsequently, a washing operation is conducted by supplying washing liquids such as water and alcohol sequentially into the reaction chamber to wash off the specimen that has not been consumed for the hybridization reaction.

The aperture section of the waste liquid reservoir 7 is pressurized by applying pressure by means of the syringe pump 12. On the other hand, the aperture section of the waste liquid reservoir 7 is put into a reduced pressure condition by reducing the pressure of the aperture section by means of the syringe pump 12. Liquid moves between the reaction chamber 4 and the liquid reservoir 5 back and forth as the pressure at the aperture section is raised and reduced alternately by means of the syringe pump 12. In other words, the liquid in the reaction chamber is agitated as the pressure at the aperture section is raised and reduced alternately by means of the syringe pump 12.

Figure 4:
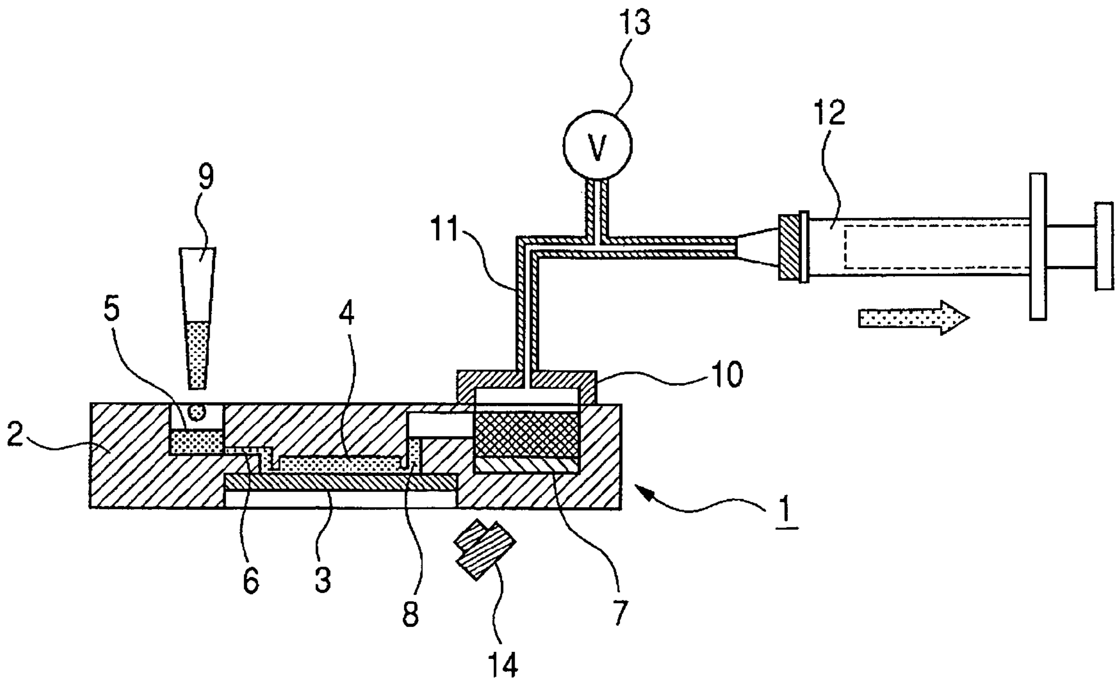
FIG. 4 is a schematic illustration of the operation of supplying solution and, at the same time, moving solution of the second embodiment of reaction cartridge according to the present invention.
Figure 5:
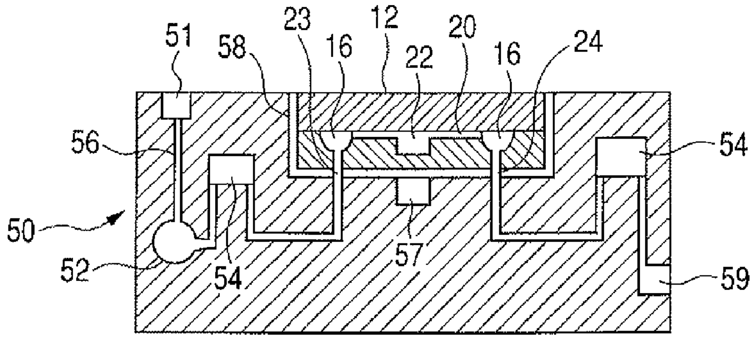
PRIOR ART FIG. 5
FIG. 5 is a schematic illustration of the conventional art.

A technique of moving liquid while supplying solution to the liquid reservoir 5 will be described below by referring to FIG. 4. Firstly, solution is supplied to the liquid reservoir 5 by means of the pipette 9 and, at the same time, the internal pressure of the syringe pump 12 is reduced to apply negative pressure to the reaction chamber 4. Thus, the solution supplied to the liquid reservoir 5 is driven to move from the liquid reservoir 5 into the waste liquid reservoir 7 by way of the reaction chamber 4.

The rate at which solution is supplied to the liquid reservoir 5 by means of the pipette 9 is made equal to or slightly higher than the rate at which liquid is driven to move from the liquid reservoir 5 to the reaction chamber 4 by means of the syringe pump 12 in order to prevent the liquid reservoir 5 from becoming empty. It is possible to use a liquid reservoir 5 having a small capacity when liquid is moved from the liquid reservoir 5, while supplying solution to the liquid reservoir 5, if compared with an arrangement where solution is supplied to the liquid reservoir first and then moving the solution after the supply.

When supplying washing liquid to the liquid reservoir 5 by means of the pipette 9, the volume of washing liquid is normally greater than the capacity of the reaction chamber 4. Washing liquid passes through the reaction chamber 4 and then through the flow channel 8 to get to the waste liquid reservoir 7.

The waste liquid reservoir 7 has an open end. However, when washing liquid is discharged to the waste liquid reservoir 7 by way of the flow channel 8, the pressure at the open end is reduced to show negative pressure. Therefore, it is possible to prevent the solution discharged from the open end of the waste liquid reservoir 7 from leaking and running into the syringe pump when an absorbent is arranged in the waste liquid reservoir 7.

Thus, the reaction cartridge to be used for biochemical reactions of this embodiment provides the following advantages.

(1) By opening either the open end of the first liquid reservoir or that of the second liquid reservoir, while closing the other, and applying negative pressure to the closed open end, it is possible to move solution supplied to the liquid reservoir having the opened open end to the liquid reservoir having the closed open end.

(2) When the open end of the first liquid reservoir is opened, firstly the solution supplied to the first liquid reservoir is moved into the reaction chamber by means of the above-described technique. Then, subsequently, it is possible to move the solution into the first liquid reservoir by applying positive pressure to the closed open end (of the second liquid reservoir) and to the second liquid reservoir by applying negative pressure.

(3) As a result, it is possible to reduce the risk of contamination among different liquids in supplying solutions of a plurality of different types from a single liquid reservoir into a reaction chamber if solutions of a large number of different types are used for reactions and processes in the substrate.

(4) Additionally, it is possible to use a first liquid reservoir having a small capacity when liquid is moved from the first liquid reservoir to the reaction chamber by means of a liquid moving means, while supplying solution to the first liquid reservoir, relative to the volume of solution to be supplied. Then, it is possible to further reduce the dimensions of the substrate.

(5) Since solutions are supplied from a single liquid reservoir and waste liquids are disposed in a single liquid reservoir so that only a single liquid moving means is required to move solutions and arranged at the side of the reaction apparatus. Thus, unlike the conventional art, it is not necessary to provide the reaction apparatus with a plurality of liquid moving means or arrange a plurality of liquid moving means in the substrate so that it is possible to simplify the mechanical section of the reaction apparatus or the configuration of the reaction cartridge.

The present invention is not limited to the above embodiments and various changes and modifications can be made within the spirit and scope of the present invention. Therefore, to appraise the public of the scope of the present invention, the following claims are made.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2005-235412, filed Aug. 15, 2005, which is hereby incorporated by reference herein in its entirety.

What is claimed is:

1. A reaction cartridge comprising:

a first liquid reservoir having a first aperture for supplying a liquid, the first aperture being exposed to the atmosphere, and a second aperture which is adapted to be prevented from communicating with the atmosphere when the first liquid reservoir is supplied with the liquid;

a first flow channel connected to the first liquid reservoir by way of the second aperture;

a reaction chamber communicating with the first liquid reservoir by way of the first flow channel;

a second flow channel connected to the reaction chamber;

a third aperture for rendering the second flow channel to communicate with the outside; and a second liquid reservoir for storing waste liquid arranged between the second flow channel and the third aperture, the cartridge being configured to move the liquid supplied to the first liquid reservoir into the reaction chamber by reducing the pressure at the third aperture and to move the liquid moved into the reaction chamber back into the first liquid reservoir by increasing the pressure at the third aperture, the second liquid reservoir being connected with the second flow channel and the third aperture respectively at higher levels than a bottom part of the second liquid reservoir so that waste liquid may be retained in the second liquid reservoir even when the pressure at the third aperture is reduced or increased.

2. The cartridge according to claim 1, wherein the cross sectional area of the first aperture is larger than the cross sectional area of the second aperture.

3. The cartridge according to claim 1, wherein an absorbent is arranged in the second liquid reservoir.

4. The cartridge according to claim 1, wherein the route of liquid flow from the second aperture to the third aperture has no branch structure.

5. The cartridge according to claim 1, wherein the route of liquid flow from the second aperture to the third aperture is not provided with an air vent.

6. The cartridge according to claim 1, wherein the first aperture is formed on an upper surface of the cartridge and the second aperture is provided at a bottom part of the first liquid reservoir.

7. The cartridge according to claim 1, wherein a probe carrier is arranged in the inside of the reaction chamber.

8. A reaction apparatus comprising:

a reaction cartridge having:

a first liquid reservoir having a first aperture for supplying a liquid, the first aperture being exposed to the atmosphere, and a second aperture which is adapted to be prevented from communicating with the atmosphere when the first liquid reservoir is supplied with the liquid;

a first flow channel connected to the first liquid reservoir by way of the second aperture;

a reaction chamber communicating with the first liquid reservoir by way of the first flow channel;

a second flow channel connected to the reaction chamber;

a third aperture for rendering the second flow channel to communicate with the outside, the third aperture being located in an upper surface of the cartridge; and a second liquid reservoir for storing waste liquid arranged between the second flow channel and the third aperture; and pressure application means for moving the liquid supplied to the first liquid reservoir into the reaction chamber by reducing the pressure at the third aperture and for moving the liquid moved into the reaction chamber back into the first liquid reservoir by increasing the pressure at the third aperture, the second liquid reservoir being connected with the second flow channel and the third aperture respectively at higher levels than a bottom part of the second liquid reservoir so that waste liquid may be retained in the second liquid reservoir even when the pressure at the third aperture is reduced or increased.

9. The apparatus according to claim 8, further comprising:

liquid supply means for supplying a liquid to the first liquid reservoir.

10. The apparatus according to claim 8, further comprising:

pressure regulation means for equalizing the pressure at the third aperture with the atmospheric pressure.

11. The apparatus according to claim 10, wherein the pressure regulation means is arranged between the third aperture and the pressure application means.

12. The apparatus according to claim 8, wherein a probe carrier is arranged in the inside of the reaction chamber.

13. A liquid moving method adapted to use a reaction cartridge having no pumping mechanism therein, the cartridge comprising:

a first liquid reservoir having a first aperture for supplying a liquid, the first aperture being exposed to the atmosphere, and a second aperture which is adapted to be prevented from communicating with the atmosphere when the first liquid reservoir is supplied with the liquid;

a first flow channel connected to the first liquid reservoir by way of the second aperture;

a reaction chamber communicating with the first liquid reservoir by way of the first flow channel;

a second flow channel connected to the reaction chamber;

a third aperture for rendering the second flow channel to communicate with the outside; and a second liquid reservoir for storing waste liquid arranged between the second flow channel and the third aperture, the method comprising:

supplying the liquid to the first liquid reservoir;

moving the liquid into the reaction chamber by reducing the pressure at the third aperture; and moving the liquid moved into the reaction chamber back into the first liquid reservoir by increasing the pressure at the third aperture, the second liquid reservoir being connected with the second flow channel and the third aperture respectively at higher levels than a bottom part of the second liquid reservoir so that waste liquid may be retained in the second liquid reservoir even when the pressure at the third aperture is reduced or increased.

14. The method according to claim 13, wherein the liquid is moved into the reaction chamber, while a liquid is simultaneously supplied to the first liquid reservoir.

15. The method according to claim 13, wherein the rate of supplying the liquid to the first liquid reservoir is equal to or greater than the rate of moving the liquid from the first liquid reservoir to the reaction chamber.

16. The method according to claim 13, wherein a probe carrier is arranged in the inside of the reaction chamber.

* * * * *